(12) United States Patent
Busnel et al.

(10) Patent No.: US 11,698,367 B2
(45) Date of Patent: Jul. 11, 2023

(54) FLOW BASED ASSAYS FOR THERAPEUTICS

(71) Applicant: Beckman Coulter, Inc., Brea, CA (US)

(72) Inventors: Jean-Marc Busnel, Marseilles (FR); Tewfik Miloud, Marseilles (FR)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 16/647,413

(22) PCT Filed: Sep. 17, 2018

(86) PCT No.: PCT/US2018/051377
§ 371 (c)(1),
(2) Date: Mar. 13, 2020

(87) PCT Pub. No.: WO2019/055938
PCT Pub. Date: Mar. 21, 2019

(65) Prior Publication Data
US 2020/0209222 A1    Jul. 2, 2020

Related U.S. Application Data

(60) Provisional application No. 62/559,261, filed on Sep. 15, 2017.

(51) Int. Cl.
*G01N 33/50* (2006.01)
*G01N 33/58* (2006.01)
*G01N 33/569* (2006.01)

(52) U.S. Cl.
CPC ..... *G01N 33/5047* (2013.01); *G01N 33/5052* (2013.01); *G01N 33/56972* (2013.01); *G01N 33/582* (2013.01); *G01N 2800/52* (2013.01)

(58) Field of Classification Search
CPC ........... G01N 33/5052; G01N 33/5047; G01N 33/582; G01N 2800/52; G01N 33/56972
See application file for complete search history.

(56) References Cited

U.S. PATENT DOCUMENTS

| 2009/0169550 A1* | 7/2009 | Dummer | A61P 19/02 424/133.1 |
| 2010/0167315 A1 | 7/2010 | Thibault et al. | |
| 2010/0221756 A1* | 9/2010 | Sainte-Laudy | G01N 33/5047 435/7.24 |
| 2015/0211064 A1* | 7/2015 | Meuer | C12Q 1/6883 435/6.11 |

(Continued)

FOREIGN PATENT DOCUMENTS

| CN | 102753195 | 10/2012 |
| WO | 2011029823 | 3/2011 |

(Continued)

OTHER PUBLICATIONS

Merkt et al. (Rituximab induces phenotypical and functional changes of NK cells in a non-malignant experimental setting. Arthritis Research & Therapy 18 (206): 1-11 (2016)—IDS.*

(Continued)

*Primary Examiner* — Gailene Gabel
(74) *Attorney, Agent, or Firm* — Schwegman Lundberg & Woessner, P.A.

(57) ABSTRACT

This invention provides methods to evaluate therapeutic efficacy of therapeutic monoclonal antibodies.

10 Claims, 13 Drawing Sheets

(56) References Cited

U.S. PATENT DOCUMENTS

| | | | |
|---|---|---|---|
| 2017/0030905 A1 | 2/2017 | Ahearn et al. | |
| 2020/0182870 A1* | 6/2020 | Basso-Ricci | G01N 33/582 |

FOREIGN PATENT DOCUMENTS

| | | |
|---|---|---|
| WO | 2017140826 | 8/2017 |
| WO | WO-2017222998 A1 | 12/2017 |
| WO | WO-2019055938 A1 | 3/2019 |

OTHER PUBLICATIONS

Findlay et al. Improved in vitro methods to predict the in vivo toxicity in man of therapeutic monoclonal antibodies including TGN1412. Journal of Immunological Methods. 352 1-23 (2010).*
Damsky et al. B cell depletion or absence does not impede anti-tumor activity of PD-1 inhibitors. Journal of ImmunoTherapy of Cancer 7 (153): pp. 1-7 (2019).*
Rudulier et al. (Modulation of CRTH2 expression on allergen-specific T cells following peptide immunotherapy. Allergy 74: 2157-2166 (2019).*
"International Application Serial No. PCT/US2018/051377, International Search Report dated Nov. 13, 2018", 5 pgs.
"International Application Serial No. PCT/US2018/051377, Written Opinion dated Nov. 13, 2018", 6 pgs.
Bezman, Natalie A, et al., "PD-1 Blockade Enhances Elotuzumab Efficacy in Mouse Tumor Models", Blood Advances, vol. 1, No. 12, (May 9, 2017), 753-765.
Bruckheimer, Elizabeth M, et al., "Antibody-Dependent Cell-Mediated Cytotoxicity Effector-Enhanced EphA2 Agonist Monoclonal Antibody Demonstrates Potent Activity Against Human Tumors", Neoplasia, vol. 11, No. 6, (Jun. 1, 2009), 509-517.
Merkt, Wolfgang, et al., "Rituximab Induces Phenotypical and Functional Changes of NK Cells in a Non-Malignant Experimental Setting", Arthritis Research & Therapy, vol. 18, No. 1, (Sep. 15, 2016).
Tembhare, Prashant R, et al., "Quantification of Expression of Antigens Targeted by Antibody-Based Therapy in Chronic Lymphocytic Leukemia", American Journal of Clinical Pathology, vol. 140, No. 6, (Dec. 1, 2013), 813-818.
"European Application Serial No. 18782855.3, Response to Communication Pursuantto Rules 161 and 162 filed Nov. 10, 2020", 11 pgs.
"International Application Serial No. PCT/US2018/051377, International Preliminary Report on Patentability dated Mar. 26, 2020", 8 pgs.
"Australian Application Serial No. 2018333062, First Examination Report dated May 25, 2021", 3 pgs.
"Canadian Application Serial No. 3,075,900, Office Action dated Apr. 23, 2021", 4 pgs.
"European Application Serial No. 18782855.3, Communication Pursuant to Article 94(3) EPC dated Jun. 24, 2021", 5 pgs.
"Indian Application Serial No. 202017015280, First Examination Report dated Apr. 28, 2021", 7 pgs.
"ReaPan 34845", Anonymous: XP55407174, Retrieved from the Internet: <http://www.demo.reametrix.comjdownload/QMS/Product Inserts/ReaPan34845.pdf>, [retrieved on Sep. 14, 2017], (Jan. 30, 2013), 1-2.
Thakar, M., et al., "CD4 estimating reagents in dry format are compatible with conventional flow cytometer; FACSCalibur for estimation of absolute CD4 count & percentages", Indian J. Med. Res .vol. 137. No. 2, (Feb. 2013), XP55406800., (Feb. 2013), 346-355.
"Australian Application Serial No. 2018333062, Response filed Jan. 12, 2022 to First Examination Report dated May 25, 2021", w/ Claims, 9 pgs.
"Canadian Application Serial No. 3,075,900 , Office Action dated Nov. 17, 2021", 6 pgs.
"Canadian Application Serial No. 3,075,900 , Response filed Mar. 17, 2022 to Office Action dated Nov. 17, 2021", 12 pgs.
"Canadian Application Serial No. 3,075,900, Response filed Aug. 20, 2021 Office Action dated Apr. 23, 2021", 12 pgs.
"European Application Serial No. 18782855.3, Response filed Oct. 14, 2021 toCommunication Pursuant to Article 94(3) EPC dated Jun. 24, 2021", 11 pgs.
"Indian Application Serial No. 202017015280, Response filed Oct. 19, 2021 to First Examination Report dated Apr. 28, 2021", 16 pgs.
"Chinese Application Serial No. 201880072707.X, Office Action dated Mar. 17, 2023", w English Translation, 31 pgs.
"Canadian Application Serial No. 3,075,900, Office Action dated Mar. 16, 2023", 7 pgs.

* cited by examiner

Various Panel Tested

| Violet Laser (405 nm) | | Blue Laser (488 nm) | | | | Red Laser (638 nm) | | |
|---|---|---|---|---|---|---|---|---|
| PB | KrO | FITC | PE | ECD | PECy5.5 | PECy7 | APC | APC-A700 APC-A750 |
| CD107a | CD45 | CD54 | CD14 | CD137 | CD19 | CD56 | CD69 | CD3 CD16 |

| Violet Laser (405 nm) | | Blue Laser (488 nm) | | | | Red Laser (638 nm) | | |
|---|---|---|---|---|---|---|---|---|
| PB | KrO | FITC | PE | ECD | PECy5.5 | PECy7 | APC | APC-A700 APC-A750 |
| INF-γ | CD45 | IL8 | IL6 | CD14 | CD19 | CD56 | CD16 | TNF-α CD3 |

| Violet Laser (405 nm) | | Blue Laser (488 nm) | | | | Red Laser (638 nm) | | |
|---|---|---|---|---|---|---|---|---|
| PB | KrO | FITC | PE | ECD | PECy5.5 | PECy7 | APC | APC-A700 APC-A750 |
| CD11b | CD45 | CC66b | CD-14-CD3 | CD62l | CD19 | CD56 | CD69 | CD11c CD16 |

Strategy
- Mimic ex vivo what can happen in vivo
- Activation of whole blood with considered biologics and flow cytometry analysis

Assays outputs
- B Cell depletion
- Activation status of NK cells
- Activation status of major leukocyte populations
- Cytokine production by leukocytes

Potential uses
➢ Predict treatment efficacy
➢ Identification of patient at risk of IRR
➢ Tools for biopharma

FIG. 1

FLOW BASED ASSAYS FOR THERAPEUTICS

CROSS REFERENCE TO RELATED APPLICATIONS

The present patent application is a U.S. National Stage Filing under 35 U.S.C. 371 from International Application No. PCT/US2018/051377, filed on Sep. 17, 2018, and published as WO 2019/055938 on Mar. 21, 2019, which application claims benefit of priority to U.S. Provisional Patent Application No. 62/559,261, filed Sep. 15, 2017, both of which are incorporated by reference in their entirety for all purposes.

FIELD OF THE INVENTION

This invention relates to methods to evaluate therapeutic efficacy of therapeutic monoclonal antibodies.

BACKGROUND OF THE INVENTION

Since they have been initially introduced by Milstein and co-workers, monoclonal antibodies have undergone a tremendous growth in the therapeutic field. As a result, there exists today a multitude of molecules approved for a wide variety of pathologies, the majority of which has been developed for oncology and auto-immune diseases. Besides the molecules that are already approved, there is an even higher number of molecules which are currently in development. In this context, we can mention novel molecules or originator molecules that cannot be compared to any molecule already approved and the molecules that are comparable in many points to molecules already approved. The latter category is the one of biosimilars or biobetters, in reference to the originator molecule.

No matter whether originators, biosimilars, or biobetters are considered, the number of players currently involved in this field has been constantly growing in the recent years. As a result, the number of molecules currently in development is large, as are the activities required to understand and characterize these molecules. In this context, scientists involved in these activities have access to a variety of technologies that can answer specific questions along the development of new drugs. These technologies can be based on in vivo and/or in vitro approaches. In comparison to in vivo approaches, in vitro ones are usually significantly more cost- and time-effective to perform. In consequence, as long as the question asked may be answered by an in vitro approach, those will be preferable. However, though the current arsenal of in vitro approaches is vast and powerful, it needs to be improved to address the variety of applications associated with the complexities of immune-based therapies.

Therapeutic monoclonal antibodies (mAbs) can have a multitude of modes of action (MOA). The main properties that influence the mode of action of a given mAb are its specificity, its isotype, and its glycosylation moieties. As a function of those, therapeutic antibodies can have an agonist or antagonist effect and/or can recruit other actors such as effector cells or complement pathways.

To study in vitro the mAbs it is developing, a biopharmaceutical industry can use a variety of techniques, ranging from tools that enable the characterization of the primary structure of the mAb to techniques that enable the characterization of its function. Herein, development of functional assays will be considered.

If the goal of a therapeutic mAb is, for example, to induce the lysis/removal of a given kind of cell, it may be directed toward an antigen that is presented at the surface of the target cell or may be directed to a soluble protein, such as a cytokine (e.g., TNFα). As a function of the antigen being chosen, direct cell lysis can be induced upon binding of the mAbs' paratopes to the antigens' epitopes. This is a first approach toward target cell removal; however this approach might not always be the most efficient or the most effective. One MOA for therapeutic mAbs relies on antibody dependent cell cytotoxicity (ADCC). In this approach, while the paratopes of the mAbs, located on the Fab section, are able to bind with the antigens of the target cells, the Fc part of the mAb is such that it enables the engagement of effector cells such as natural killer (NK) cells through binding with their Fc receptor molecules. Upon bridging, the effector cells will release a variety of mediators, which induce the lysis of the target cells and/or the further recruitment of other cells that may subsequently participate to the lysis/removal of the target cells.

Studying the previously described phenomenon is complex as it involves different kind of cells, including at least the target and the effector cells. Most strategies currently being used enable the study of only one kind of cell at a time. There are several reasons for this: the most obvious is that such approach is easier to develop and to standardize. Another aspect of the currently used solution is that they do not always account for patient heterogeneity and specificity. As a result, while they are useful in a biopharmaceutical context when the aim of the experiment is to study a given mAb under a set of very standardized conditions, they are of limited interest when finer characterization of the mAbs and/or patient stratification is being pursued.

If the focus is on mAbs that rely on the ADCC MOA, the most commonly used approach for comparing the capability of mAbs to induce ADCC is the Chromium 51 ($^{51}$Cr) release assay. In this approach, target cells are loaded in vitro with radioactive Chromium 51 and placed in presence of effector cells (cell lines or PBMC) and therapeutic mAbs. The assay provides a quantitative measure of the cytotoxicity by reading out, after a given incubation time, the amount of Chromium 51 released in the supernatant.

While the target cells used in this assay most commonly originate from cell lines expanded in vitro, the effector cells can be originated from cell lines or donor/patient's PBMCs as a function of the pursued objectives. Although this approach may provide some advantages, such as parallel processing, sensitivity, reproducibility, etc., it also presents major disadvantages such as the use of radioactive materials. For this reason, alternate methodologies that rely on other detection technologies such as fluorescence or luminescence have been proposed. Another major disadvantage is its poor compatibility with whole blood samples. As a result, when patient heterogeneity has to be taken into account for drug development and/or in the context of patient stratification, the labor-intensivity and the cost of having to prepare PBMCs can quickly be a limiting factor. Further, the large number of steps prior to reading the output of the assay makes these strategies complex and tedious to perform, ultimately leading to high variability and poor reproducibility.

The ADCC reporter assay from Promega is a commercial alternative to the $^{51}$Cr release assay. This approach relies on the use of engineered NK cell lines provided in a frozen format that simply needs to be thawed for use. These cell lines are engineered to express luciferase through the NFAT signaling pathway upon ADCC. As compared to classic $^{51}$Cr release assays, this approach is free of radioactive materials and removes the effector cells-related variability from the overall assay variability. As a result, this approach is useful as long as donor/patient heterogeneity need not to be taken into account of if no fine characterization of the NK cell response (which mediators are released and in which quantity) is needed.

No matter whether the classic $^{15}$Cr assay or the ADCC reporter assay is considered, a major limitation of these strategies is that they provide a single read-out parameter which may not be sufficient. When the objectives include fine characterization of the response (such as in assessing the comparability of various mAbs or patient stratification for treatment personalization) such single read-out parameters cannot provide a complete characterization of the response.

When patient's heterogeneity has to be taken into account or when a finer characterization of the activation status is required, flow cytometry based techniques are useful as these approaches provide high flexibility and the fine characterization capabilities. The contents of the assay can be tuned to fit the need of most specific cases, and the amount of information provided can be large because multi-color flow cytometry provides for simultaneous measurement of multiple parameters.

Most of the approaches currently used and commercialized for the study of ADCC rely on the use of cell lines, either effector or target cells. In such a case, they may present the advantage of being standardizable and relatively robust but don't account for patient heterogeneity. They reach their limits when the in vitro approach is developed to match as much as possible with situations encountered in vivo. If some of the previous methods, such as the $^{51}$Cr release assay can also be performed with PBMCs, and as a result take into account patient heterogeneity, they rapidly become very much labor-intensive and prone to variability.

When flow cytometry solutions are being developed to fulfill the above requirements, these approaches are highly "artisanal." They are not well compatible with clinical research studies that may require multi-centric analyses and longitudinal follow-up.

No matter which of the approach is considered, all currently commercialized techniques rely on reagents whose storage should be well controlled (2-8° C., −20 or −90° C.) and require multiple pipetting steps. These storage and processing requirements impose significant limitations for ready-to-use solutions. For example, the ADCC reporter assay from Promega is provided in a thaw-and-use format but, as mentioned above, does not allow a path toward patient stratification. No solution available today is personalized to the extent that a patient-specific question can be answered.

The present invention addresses these and other needs.

SUMMARY

In embodiments, the invention includes a method of evaluating a reaction to therapy. The method includes steps of exposing blood cells from a patient to a therapeutic antibody, combining the exposed blood cells with a plurality of labeled reporters to produce labeled cells, measuring signals from the labeled cells, and combining the measured signals into an assay output. The assay output is indicative of the patient's reaction to the therapeutic antibody.

The method may include as an assay output one or more of target cell (e.g., B cell) depletion, activation of white cell subpopulations, or cytokine production by white cells. The white cell subpopulations may include NK cells. The plurality of labeled reporters may include a cell surface marker and a cytokine. Among these reporters may be antibodies to CD137 and to CD69 and antibodies to TNF-α and to IL8. Other labeled reporters may include antibodies to CD66b and CD11c or antibodies to CD63, CD3, CD19, CD56, CD54, CD107a, CD107b, CD11b, INF-γ, IL6, and CD45.

In some embodiments, the therapeutic antibody targets a soluble protein, such as a cytokine (e.g., TNF α). In these embodiments, blockade of the mechanisms mediated by the soluble protein are detected.

In other embodiments, the invention includes a method of evaluating response to therapeutic antibodies having steps of exposing a first aliquot of blood cells to a first therapeutic antibody and a second aliquot of blood cells to a second therapeutic antibody. Each aliquot may be combined with respective pluralities of labeled reporters to produce a first aliquot of labeled cells and a second aliquot of labeled cells. Signals may be measured from the labeled cells of each aliquot in a flow cytometer. A step of evaluating the measured signals determines a cellular response to the first therapeutic antibody and to the second therapeutic antibody.

In some embodiments, the plurality of labeled reporters includes labeled antibodies against CD107a, CD69, and CD54, and wherein the blood cells include one or more of NK cells, neutrophils, basophils, and monocytes.

In yet other embodiments, the invention includes a method of characterizing a biopharmaceutical agent. The method includes steps of assaying a functional response of a blood cell to the biopharmaceutical agent and comparing the functional response of the blood cell to that of a reference composition. The biopharmaceutical agent may be characterized by the functional response with respect to that of the reference composition.

The step of assaying may include combining the blood cell with a plurality of labeled reporters, and measuring signals from the blood cell in a flow cytometer. The plurality of labeled reporters may include labeled antibodies against CD107a, CD69, and CD54. The blood cell may include an NK cell, a monocyte, or a mixture of cell types. In embodiments, the plurality of labeled reporters may include a labeled antibody that binds to a surface marker of the blood cell.

In other embodiments, (or in addition), the plurality of labeled reporters may include a labeled antibody to a cytokine.

BRIEF DESCRIPTION OF THE DRAWINGS

FIG. 1 is a summary that highlights (in colored boxes) the markers that produced good results in the assays of the invention.

DETAILED DESCRIPTION

Figure 2:
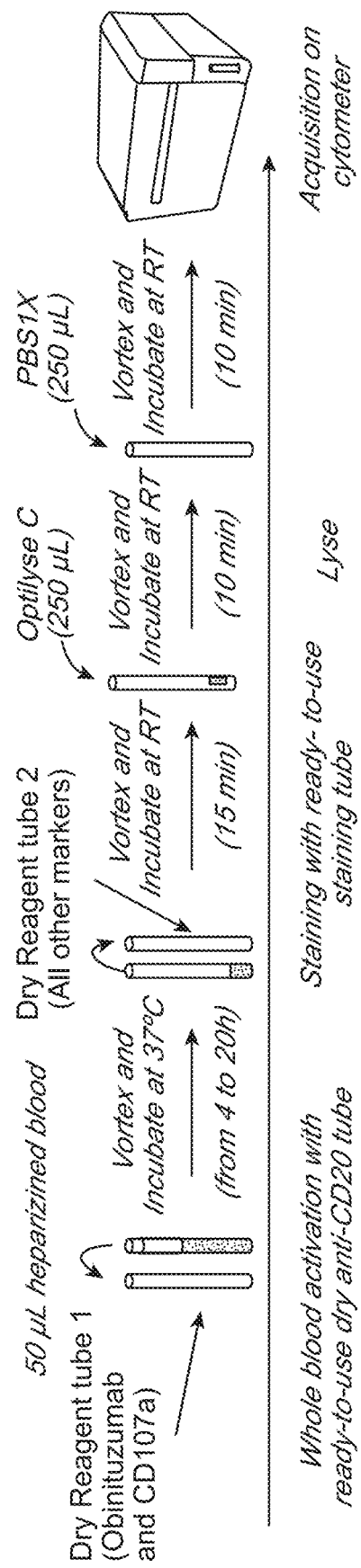
FIG. 2 illustrates steps of performing methods of the invention showing a short and simple user operations.

The present invention provides an approach based on the use of dry and room temperature stable reagents that enable whole blood sample analysis. In particular, the invention provides a ready-to-use approach for studying by flow cytometry the effect or function of a given therapeutic mAb (or any other biologics) on a given whole blood sample. In one embodiment, both staining reagents (fluorochrome conjugated antibodies) and therapeutic agents (therapeutic mAb or any other biologic) are provided in a dry, room temperature stable and ready-to-use format. In this case, only whole blood needs to be added in the dry reagent tube/container, which makes the assays of the invention very simple and highly standardizable, and therefore highly desirable in clinical research settings. The invention can be of interest in various situations, whether it deals with mAb characterization or patient stratification.

Anti-CD20 Antibodies

To illustrate the use and interest of the invention, the case of anti-CD20 therapeutic mAbs is considered here. One skilled in the art would readily appreciate that the method and composition disclosed herein can be used to study the effect or function of any therapeutic antibody or agent. Non-limiting examples of such therapeutic antibodies and agents include Anti-CD38, anti-CD19, anti-PDL1, and anti-PD1 antibody. It is a relevant study case as there is today a lot of activity around this category of mAbs. Anti-CD20 mAbs are currently used to treat various pathologies, from B-cell lymphoma to auto-immune diseases and have been commercialized for more than 15 years.

Different challenges are currently encountered in the field of anti-CD20 therapies. The first challenge is that biosimilars to rituximab, the first anti-CD20 therapeutic mAb to be approved in 1997, can now be commercialized once developed, tested, and approved. Several companies may attempt to develop biosimilars to this molecule, because Rituximab annual revenues are very large (greater than $7B). The availability of tools that would enable a fine comparison between several molecules is thus crucial. A second challenge is related to patient stratification and treatment personalization. Several therapeutic mAbs targeting the CD20 antigen are on the market and more molecules (biosimilars, biobetters or other originators) are in their later phases of development. Thus more than one anti-CD20 molecule could be chosen to treat a given patient. Putting aside biosimilars that should behave similarly, a doctor must best determine the anti-CD20 therapeutic mAb to be used for a given patient. Indeed, as a function of the mAb chosen, not only the success of the therapy can vary but also the magnitude and the potential gravity of the side effects. A particular side effect is called "infusion related reactions" (IRR). It occurs for some patients while treated with Rituximab and much more frequently (>10%) when Obinituzumab is being used. These IRRs may be very violent, potentially fatal, side reactions and may include anaphylactic shock or cytokine release syndrome (CRS). CRS is caused by a large, rapid release of cytokines into the blood from immune cells affected by the immunotherapy. Signs and symptoms of cytokine release syndrome include fever, nausea, headache, rash, rapid heartbeat, low blood pressure, and trouble breathing. It is of the great importance to be able to predict the occurrence of such reaction for a given individual so that the treatment can be modified to limit the risk as much as possible.

While the capability to predict success, failure, or side effects is crucial for patient stratification and treatment personalization, it is also very important in the context of biopharmaceutical development.

The present invention has been developed to potentially answer the previously described questions. Schematically, it has been developed so that what could happen in vivo could be mimicked in vitro while only relying on a very simple and straightforward experimental procedure. These objectives could be leveraged for both patient stratification and therapeutic mAb comparability assessment.

We have prepared several cytometry panels to address different objectives.

TABLE 1

| Extracellular panel | | | | | | | | | |
|---|---|---|---|---|---|---|---|---|---|
| Violet Laser (405 nm) | | Blue Laser (488 nm) | | | | | Red laser (638 nm) | | |
| PB | KrO | FITC | PE | ECD | PECy5 | PECy7 | APC | APC-A700 | APC-A750 |
| CD107a | CD45 | CD54 | Mix of KIRs | CD16 | CD19 | CD69 | CD314 | CD56 | CD3 + CD14 |

The above extracellular panel (Table 1) enables the concomitant monitoring of B cell depletion as well as NK cell activation upon a stimulation with (for example) an anti-CD20 therapeutic antibody. In the present format, both the staining reagents and the therapeutics are ready to be used in the sample vials as dry reagents and blood simply needs to be added before incubation at 37° C. to start the assay.

Labeled reporters (typically fluorescently-labeled antibodies) directed against cellular components CD45, CD19, CD56, CD3, CD14, and a Mix of killer immunoglobulin-like receptors (KIRs), are gating reagents while labeled reporters directed against CD107a, CD69, and CD54 help characterize the activation status of both NK cells and monocytes (CD69 and CD54). The first row of the above panel shows a laser used to excite the fluorescent dye associated with each labeled reporter. The lasers and labels of this example are adjusted to match those of available variants of the Applicant's CytoFLEX cytometer. The second row indicates the label associated with each labeled reporter; the third row indicates specificity: the cellular components against which the labeled reporter is directed.

Figure 3:
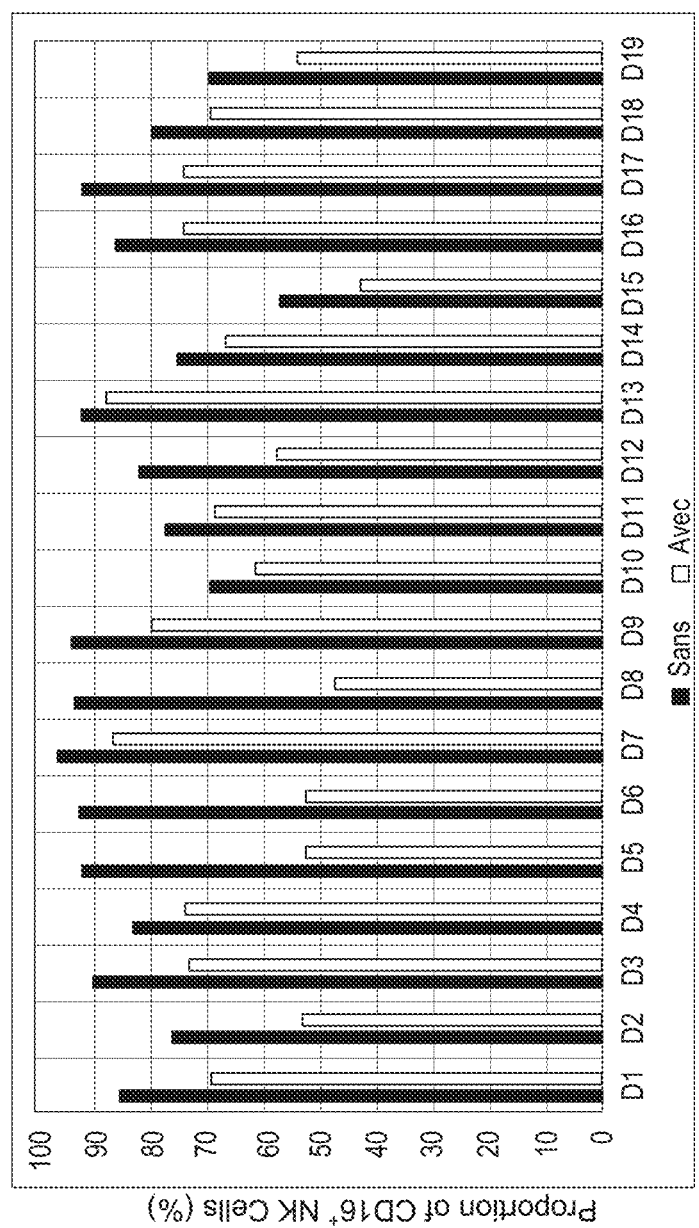
FIG. 3 shows variations of expression of CD16 on NK cells from various donors with and without treatment by Obinituzumab.

FIG. 3 shows variations between cells from different donors with and without treatment by Obinituzumab. The cells were analyzed using the extracellular panel described above and measured in a CytoFLEX cytometer gating to isolate NK cells. The bars show the expression of CD16 on NK cells from various donors. Note the very heterogeneous ability of NK Cells to internalize CD16 upon binding with Obinituzumab.

Figure 4:
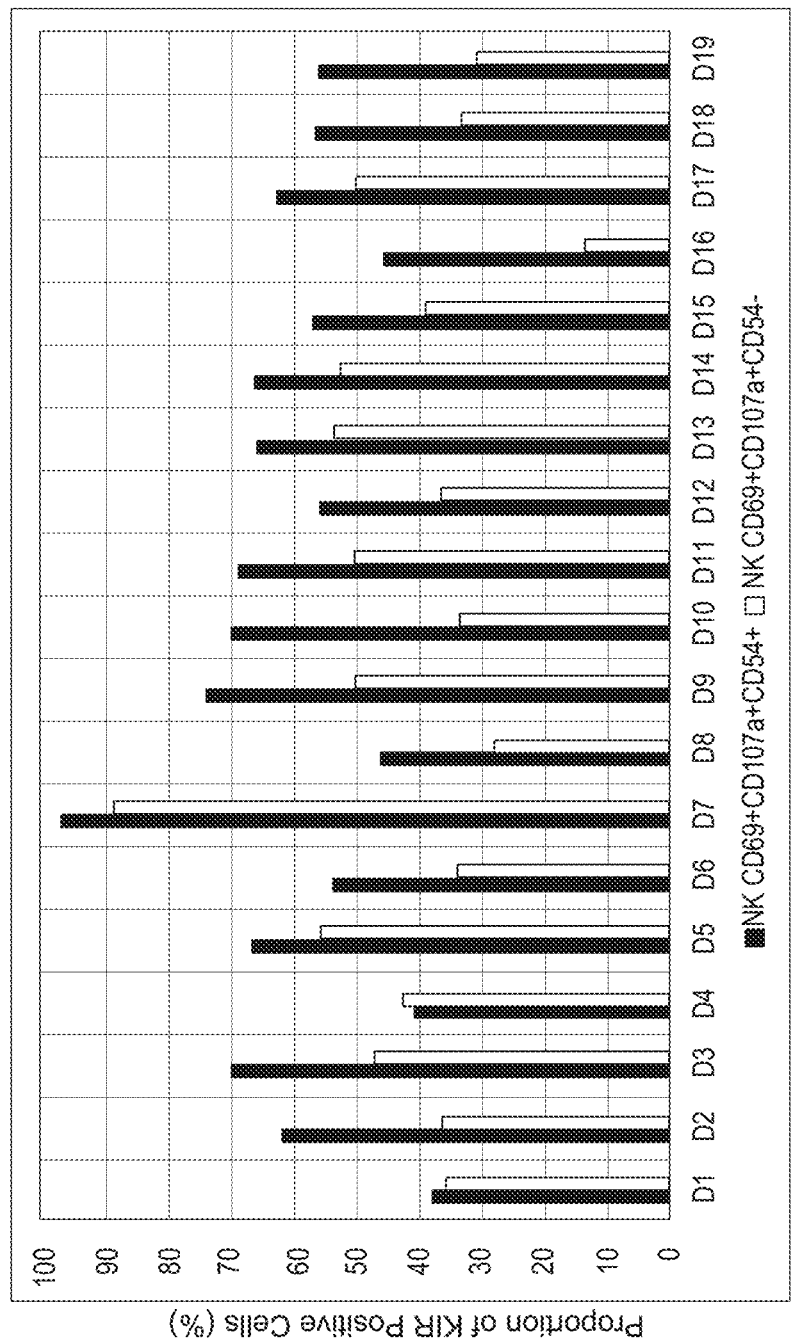
FIG. 4 shows variations of KIR positivity between NK cells from the same set of donors with and without treatment by Obinituzumab using the extracellular panel used in FIG. 3.

FIG. 4 shows variations between cells from the same set of donors using the same extracellular panel described above. When compared to resting NK cells, fully activated NK cells present a higher percentage of KIR positive cells. This illustrates in part the utility of different assay outputs even with the same panel.

The results of tests for extracellular markers showed the following. A large heterogeneity of response between the different donors tested was seen. There was no apparent correlation between studied parameters and magnitude of B cell depletion. The percentage of triply positive NK cells (CD69$^+$CD107a$^+$CD54$^+$) was most correlated with activation. Fully activated NK cells were significantly more KIR positive than the resting ones.

An intracellular panel of the invention is presented in Table 2 above; the description of each line of the table is the same as that for the extracellular panel. As in the case of the extracellular panel, the intracellular panel has been developed to enable the concomitant monitoring of B cell depletion as well as NK cell activation upon a stimulation with an anti-CD20 therapeutic antibody. It is not presently known which cytokines and/or which cell types are the most responsible for IRRs. It is interesting to mention that therapeutic mAbs/fusion protein the cytokines followed here do already exist. If it is found that one of the cytokines is more particularly responsible for potential IRRs in a given patient, the appropriate drug to counter that cytokine effect could be added to the therapeutic cocktails of the considered patient to minimize the probability of the occurrence of IRRs. Likewise, the present invention can be used to determine whether one of the cytokines is more particularly responsible for the cytokine release syndrome (CRS) in a given patient, and the appropriate drug to counter that cytokine effect could be administered to the patient.

As in in the case of the extracellular panel, a large heterogeneity of response between the different donors tested was observed. Three main profiles have been identified when focusing on monocytes (n=13): donors mainly expressing IL8 (n=10), donors mainly expressing IL8 and IL6 (n=2) and donors mainly expressing IL8 and TNFα (n=1). No IL10 expression was observed on monocytes under the tested conditions. Production of IFN and TNFα observed on NK cells but required brefeldine conditions different from monocytes.

Considering that anaphylactic shocks are also listed as potential IRR a panel in Table 3 below (including CD203c, CD63, CD3, CRTH2, and CD45) to determine basophil activation is also useful to characterize the basophil activation status upon therapeutic mAb stimulation, especially when considering mAbs with murine amino acid sequences and/or glycosylation moieties.

TABLE 2

| Intracellular Panel | | | | | | | | | |
|---|---|---|---|---|---|---|---|---|---|
| | | | | | | | | Red laser (638 nm) | |
| Violet Laser (405 nm) | | Blue Laser (488 nm) | | | | | APC- | APC- | |
| PB | KrO | A488 | PE | ECD | PECy5 | PECy7 | APC | A700 | A750 |
| IFNγ | CD45 | IL8 | IL6 | CD16 | CD19 | CD3 + CD14 | IL10 | TNFα | CD56 |

TABLE 3

| Violet Laser (405 nm) | | | Blue Laser (488 nm) | | | | Red laser (638 nm) | | |
|---|---|---|---|---|---|---|---|---|---|
| PB | KrO | FTTC/ A488 | PE | ECD | PECy5 | PECy7 | APC/ A647 | APC-A700 | APC-A750 |
| CD63 | CD45 | CD3 | CD203c | | | | CDTH2 | | |

To help the model to be finalized, additional information such as CD16 variant might be needed for each patient and future experiments will help us characterize the importance of each of the above panels.

Another set or extracellular and intracellular panels useful in the invention are presented in Tables 4 and 5, below.

TABLE 4

Extracellular panel

| VIOLET LASER (405 NM) | | BLUE LASER (488 NM) | | | | | RED LASER (638 NM) | | |
|---|---|---|---|---|---|---|---|---|---|
| PB | KrO | FITC | PE | ECD | PEcy5.5 | PECy7 | APC | APC-A700 | APC-A750 |
| CD107a | CD45 | CD54 | CD14 | CD137 | CD19 | CD56 | CD69 | CD3 | CD16 |

TABLE 5

Intracellular Panel

| VIOLET LASER (405 NM) | | BLUE LASER (488 NM) | | | | | RED LASER (638 NM) | | |
|---|---|---|---|---|---|---|---|---|---|
| PB | KrO | FITC | PE | ECD | PEcy5.5 | PECy7 | APC | APC-A700 | APC-A750 |
| INFγ | CD45 | IL8 | IL6 | CD14 | CD19 | CD56 | CD16 | TNFα | CD3 |

Figure 5:
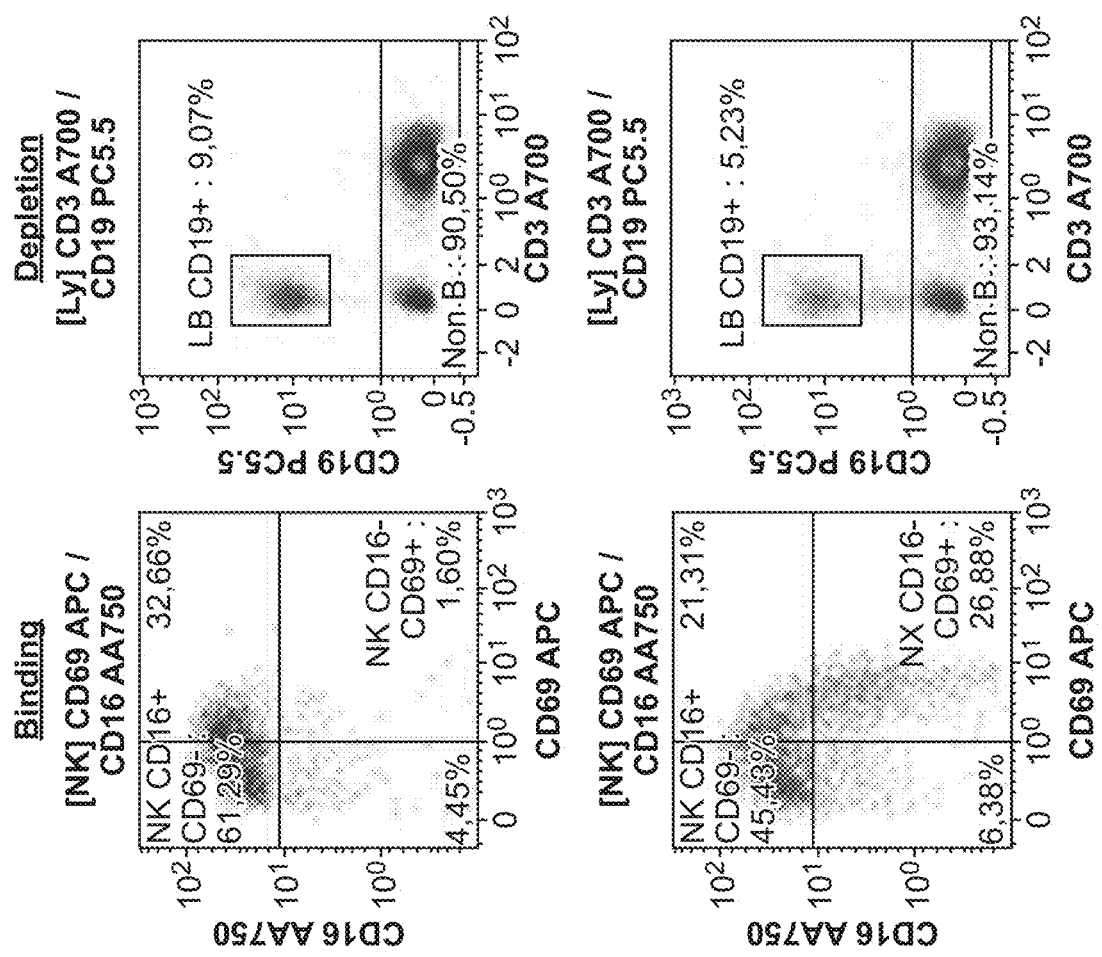
FIG. 5 shows the ability of the methods of the invention to assess the function of an anti-CD20mAb. The top panel shows the results of assays in the absence of mAb and the bottom panel shows the results of assays in the presence of mAb.
Figure 5A:
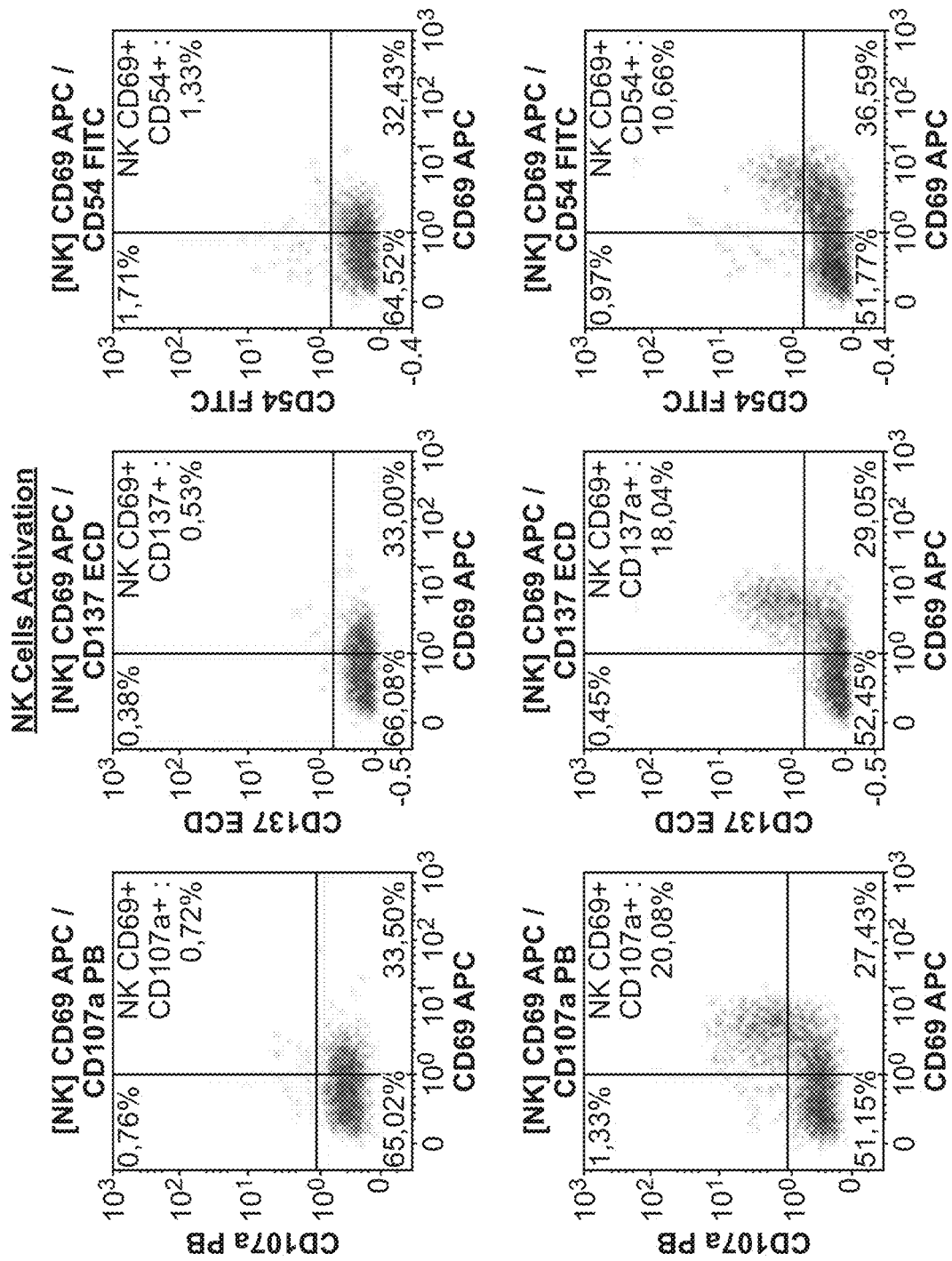
Figure 6:
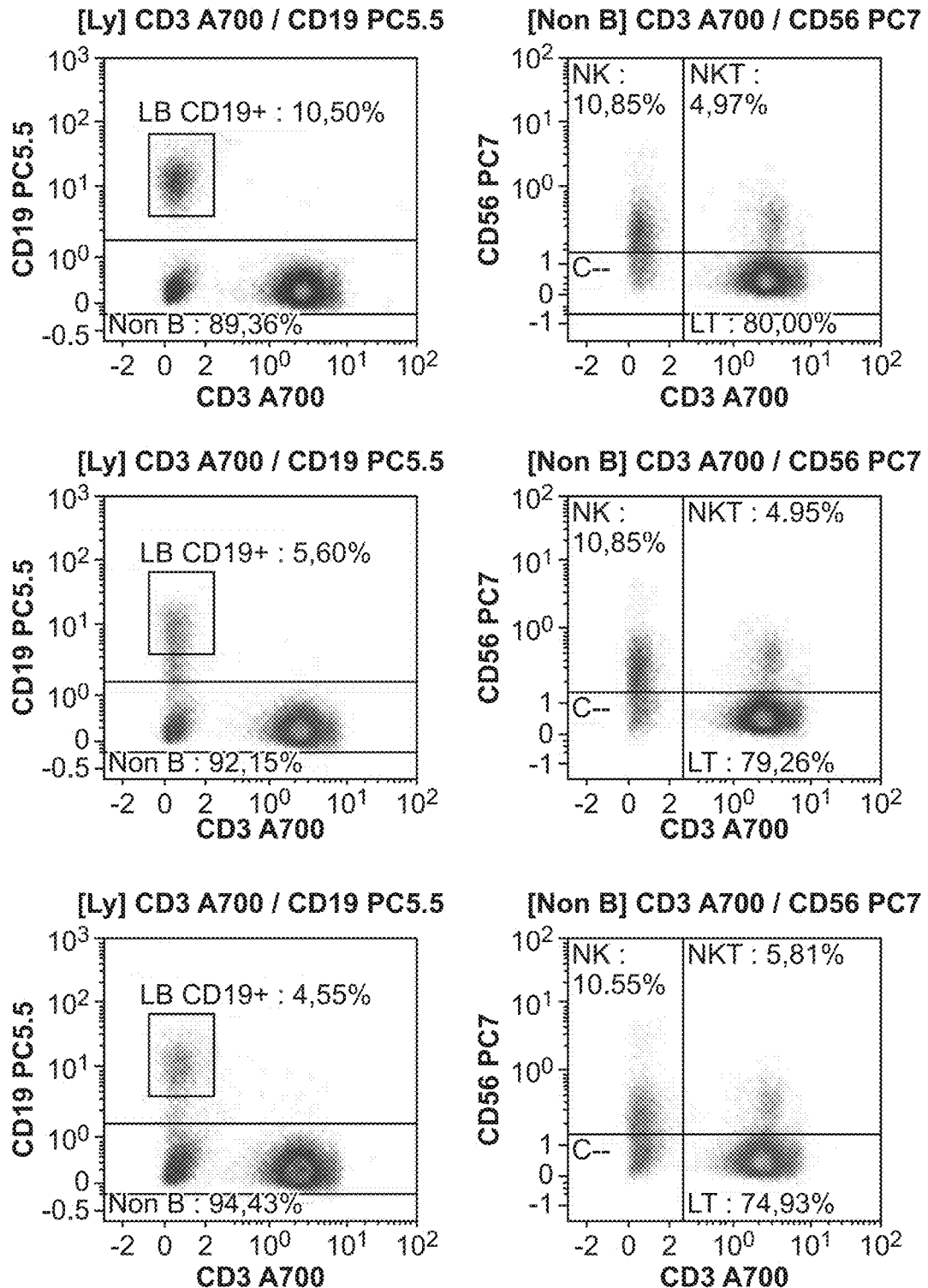
FIG. 6 shows ability of the methods of the invention to compare different mAbs. The top panel shows the results of assays in the absence of mAb, panel shows the results of assays in the presence of Rituximab and the bottom panel shows the results of assays in the presence of Obinutuzumab. The results show the same magnitude of B cell depletion with both mAbs. OBI however is shown to be more potent in engaging NK cells.
Figure 6:
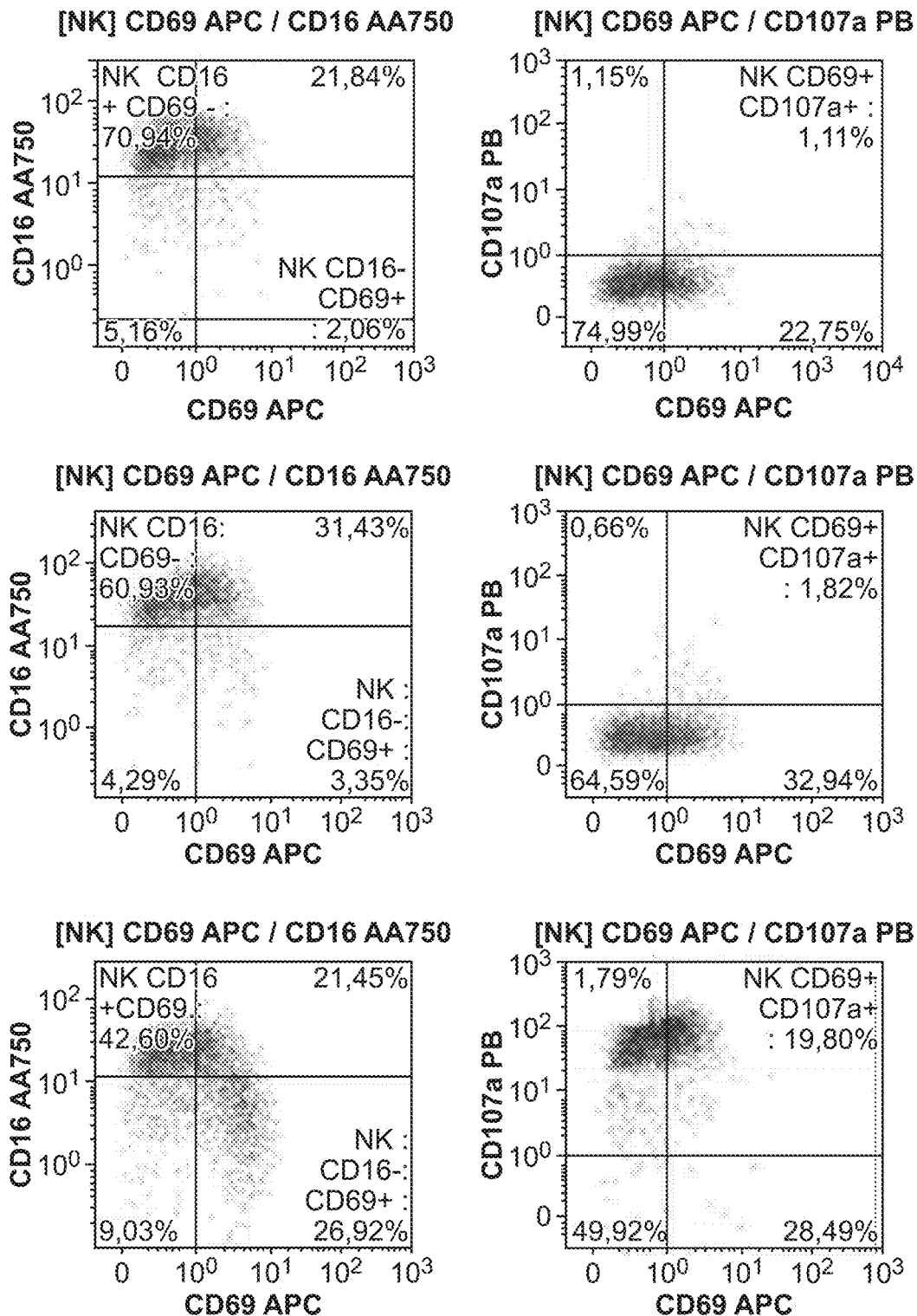

The ability to assess the function anti-CD20 mAb using the above panels is shown in FIG. 5.

Anti-TNFα Antibodies

Figure 7:
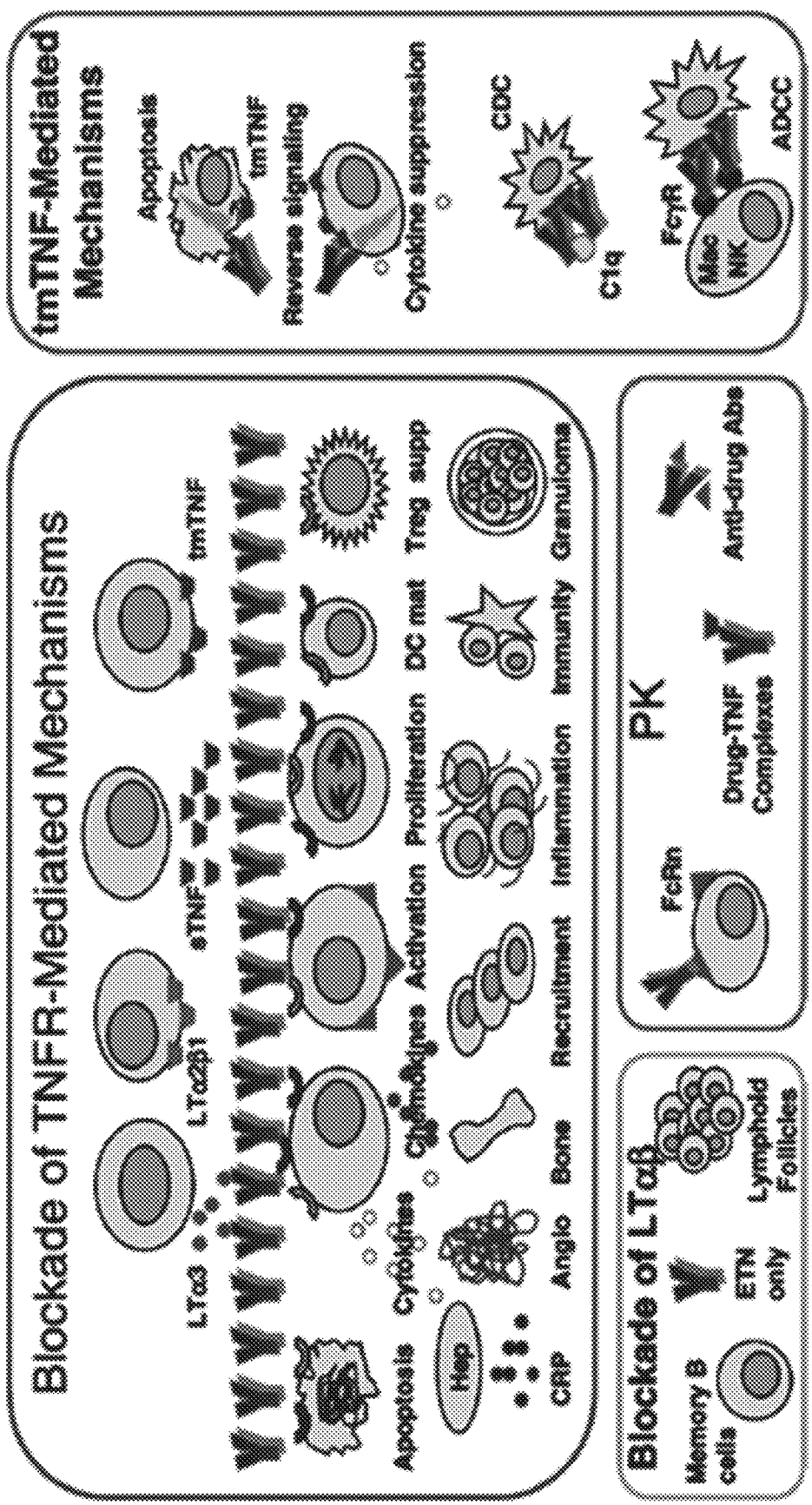
FIG. 7 shows the mechanisms of actions mediated by soluble (sTNF) and membrane-bound (tmTNF).

The approach demonstrated above can also be applied to soluble molecules, such as TNFα. The mechanisms of actions mediated by soluble (sTNF) and membrane-bound (tmTNF) are illustrated in FIG. 7. The methods of the invention can be used, for example, to stratify patients and personalize patients over time. Panels useful for Anti-TNFα mAbs are presented in Tables 6 and 7.

TABLE 6

Extacellular panel

| VIOLET LASER (405 NM) | | BLUE LASER (488 NM) | | | | | RED LASER (638 NM) | | |
|---|---|---|---|---|---|---|---|---|---|
| PB | KrO | FITC | PE | ECD | PEcy5.5 | PECy7 | APC | APC-A700 | APC-A750 |
| CD3 | CD45 | CD54 | TNFR2 | CD 14 | CD19 | CD56 | CD69 | TNF | CD16 |

TABLE 7

Intracellular Panel

| VIOLET LASER (405 NM) | | BLUE LASER (488 NM) | | | | | RED LASER (638 NM) | | |
|---|---|---|---|---|---|---|---|---|---|
| PB | KrO | FITC | PE | ECD | PEcy5.5 | PECy7 | APC | APC-A700 | APC-A750 |
| IL10 | CD45 | IL8 | IL6 | CD14 | CD3 | CD56 | CD69 | TNF | CD16 |

Figure 8:
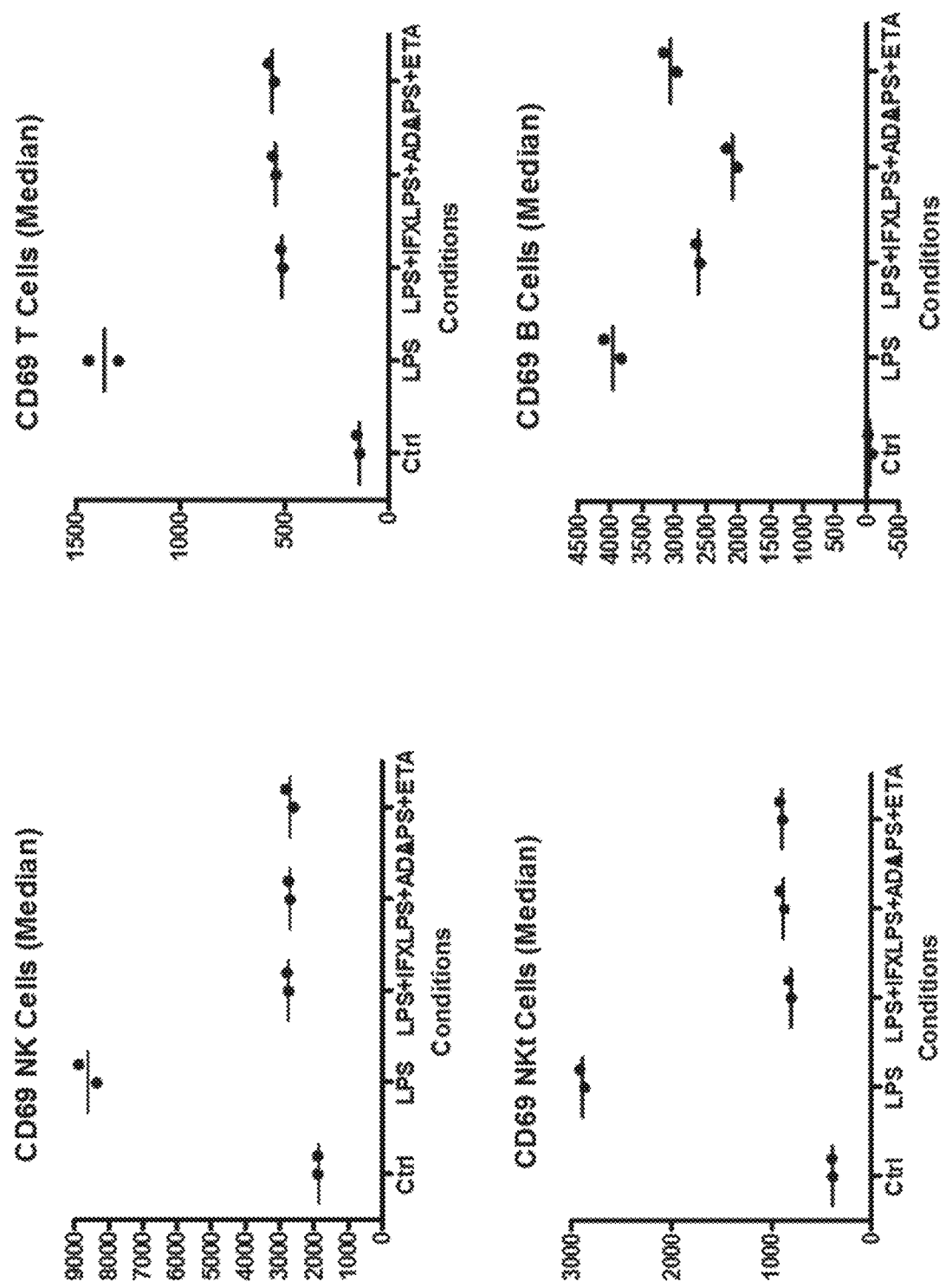
FIG. 8 shows the results of assays of the invention using the extracellular panel for three different anti-TNF biologics-infliximab (IFX), adalimumab (ADA) and etanercept (ETA) used to block soluble TNF.
Figure 9:
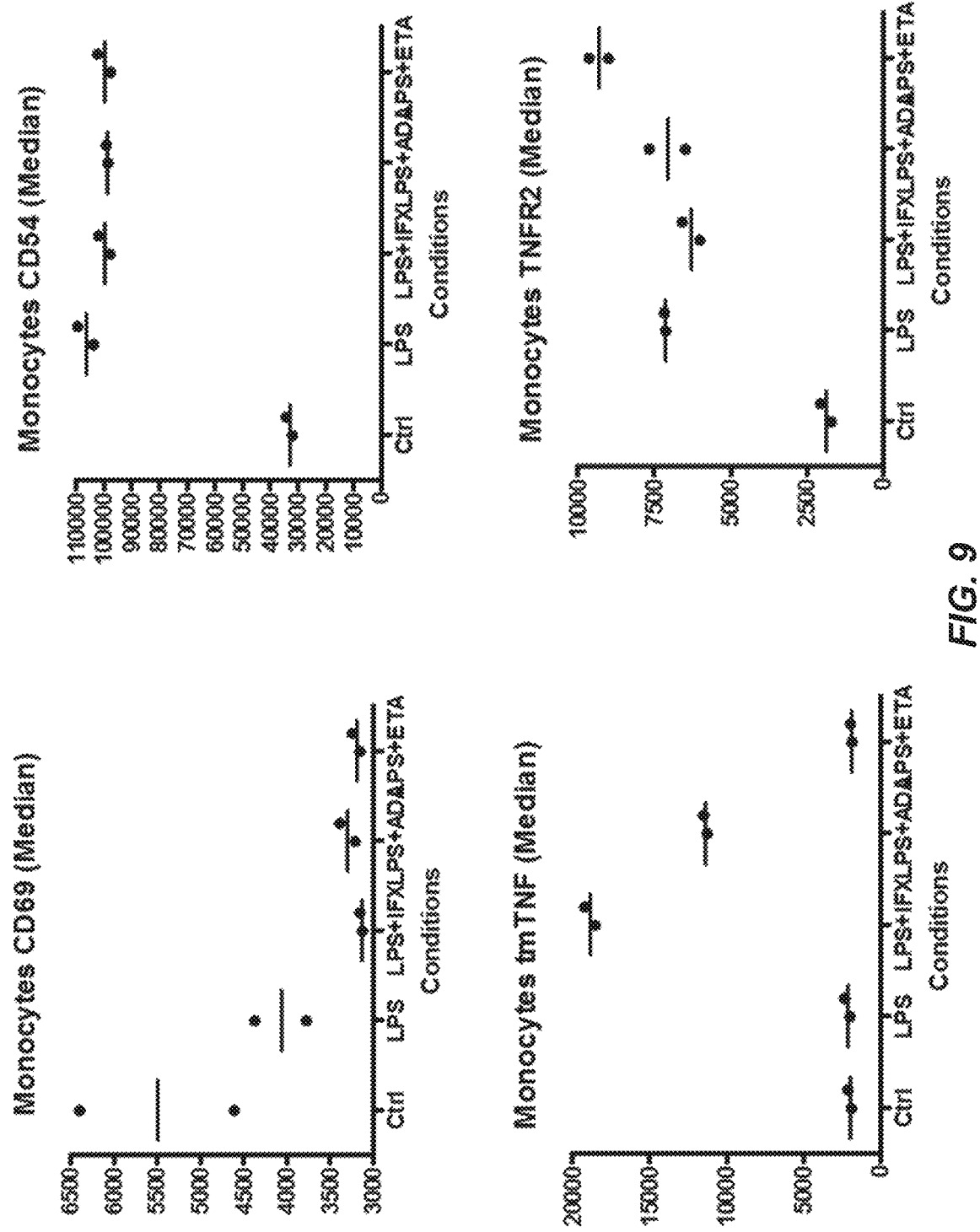
FIG. 9 shows the results of assays of the invention using the extracellular panel for three different anti-TNF mAbs-IFX, ADA and ETA used to block membrane bound TNF.
Figure 10:
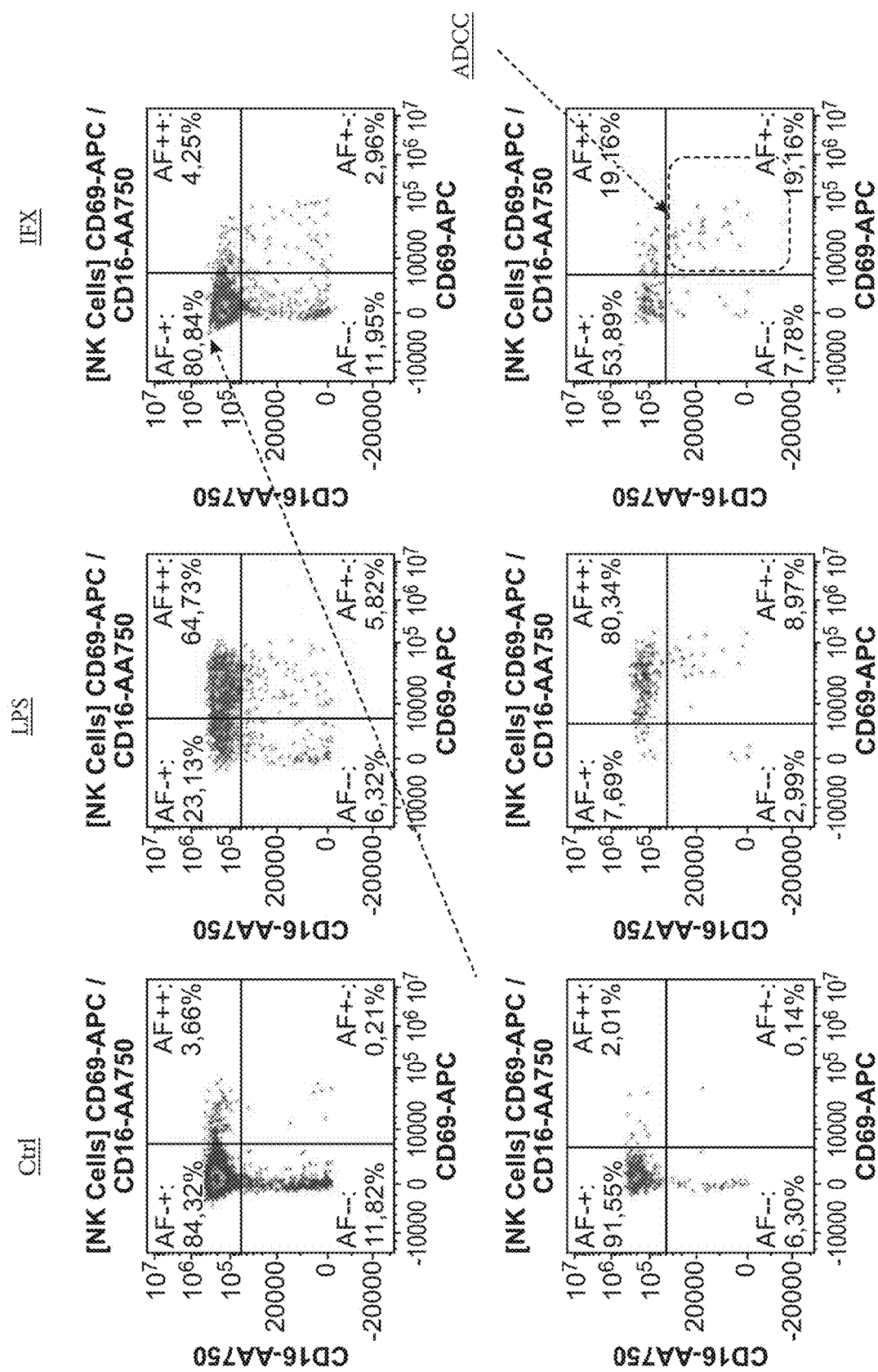
FIG. 10 shows the results of assays to monitor ADCC using the extracellular panel for three different anti-TNF mAbs-IFX, ADA and ETA. The top panels are the results from 4 hours after addition of one of the therapeutic antibodies (IFX, ADA, or ETA), showing the depletion of soluble TNF. The lower panel are the results from 4 hours after addition of one of therapeutic antibodies, showing ADCC response in the lower right quadrant.
Figure 10:
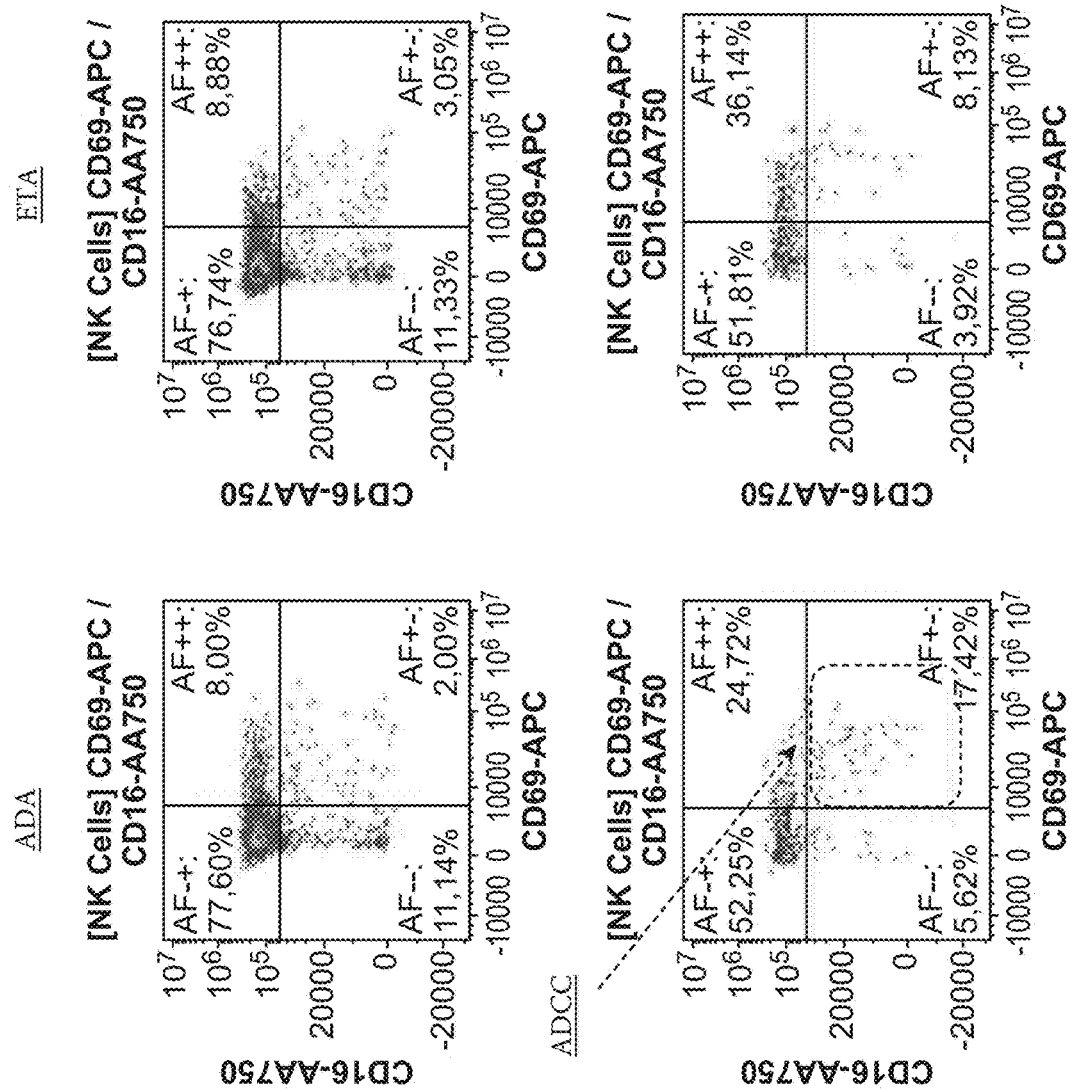

The results of assays using these panels to monitor various mechanisms of action are shown in FIGS. 8-10.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A flow cytometry method of analyzing an immune reaction to a therapeutic antibody of a patient in vitro, the therapeutic antibody being capable of multiple modes of action so that it will bind a cell depletion surface marker to effect lysis and enable engagement of effector cells, the method comprising:
    exposing a whole blood sample from a patient to the therapeutic antibody in dry reagent form;
    combining exposed blood cells from the whole blood sample with a panel of a plurality of labeled reporters comprising at least two labeled reporters selected from the group consisting of a labeled reporter directed against a target cell depletion surface marker, a labeled reporter directed against an activation surface marker expressed on white blood cell populations, and a labeled reporter directed against cytokine production by white blood cells to thereby simultaneously produce assay signals generated by the at least two labeled reporters;
    subjecting the blood cell sample mixture to flow cytometry and measuring signals generated by each of the plurality of labeled target cells and labeled cytokine; and
    combining the measured signals into an assay output for flow cytometric multiparameter analysis, the assay output indicative of the patient's immune reaction to the therapeutic antibody and the assay output providing simultaneous differentiation between signals generated by the at least two labeled reporters associated with one or more of target cell depletion, activation of white blood cell subpopulations, and cytokine production by the white blood cells.

2. The method of claim 1, wherein the target cell is a B cell.

3. The method of claim 2, wherein the therapeutic antibody in dry reagent form binds to at least one antigen selected from the group consisting of CD20, CD38, CD19, programmed death-ligand 1 (PDL1), and programmed cell death protein 1 (PD1).

4. The method of claim 1, wherein the white blood cell subpopulations comprise natural killer (NK) cells.

5. The method of claim 1, wherein the therapeutic antibody in dry reagent form binds a cytokine.

6. The method of claim 1, wherein the plurality of labeled reporters directed against an activation surface marker expressed on white blood cell subpopulations comprises antibodies to CD137, to CD69, or a combination thereof.

7. The method of claim 1, wherein the plurality of labeled reporters comprises antibodies to a cytokine including interferon gamma (INF-γ) to interleukin-8 (IL8), to TNF-α, to interleukin-6 (IL-6), to interleukin-10 (IL-10), or a combination thereof.

8. The method of claim 1, wherein the plurality of labeled reporters directed against a surface marker of activation of white blood cell subpopulations comprises antibodies to CD66b, CD11c, or a combination thereof.

9. The method of claim 1, wherein the plurality of labeled reporters directed against a surface marker of activation of white blood cell subpopulations comprises antibodies to CD203c, CD63, CD3, chemoattractant receptor-homologous molecule expressed on Th2 cells (CRTH2), and CD45.

10. The method of claim 1, wherein:
    the therapeutic antibody binds to at least one antigen to generate a signal associated with target cell depletion, the at least one antigen comprising CD19, CD38, tumor necrosis factor alpha (TNFα), PD-1, PD-L1, CRTH2, or a mixture thereof;
    the therapeutic antibody binds to at least one antigen to generate a signal associated with activation of white blood cell subpopulations, the at least one antigen comprising CD69, CD107a, CD54, CD137, CD66b, CD11b, CD11 c, TNFα, CD203c, CD16, CRTH2, or a mixture thereof;
    the therapeutic antibody binds to at least one antigen to generate a signal associated with cytokine production by white blood cells, the at least one antigen comprising IFNγ, TNFα, IL-6, IL-8, IL-10, or a mixture thereof; or
    a mixture thereof.

* * * * *